(12) United States Patent
Wellhoefer

(10) Patent No.: US 9,861,275 B2
(45) Date of Patent: Jan. 9, 2018

(54) APPARATUS, INTERFACE UNIT, SUCTION RING AND METHOD TO MONITOR CORNEAL TISSUE

(71) Applicant: WAVELIGHT GMBH, Erlangen (DE)

(72) Inventor: Armin Wellhoefer, Schwaig (DE)

(73) Assignee: Wavelight GMBH, Erlangen (DE)

( * ) Notice: Subject to any disclaimer, the term of this patent is extended or adjusted under 35 U.S.C. 154(b) by 100 days.

(21) Appl. No.: 14/369,917

(22) PCT Filed: Dec. 20, 2012

(86) PCT No.: PCT/EP2012/076300
§ 371 (c)(1),
(2) Date: Jun. 30, 2014

(87) PCT Pub. No.: WO2014/094853
PCT Pub. Date: Jun. 26, 2014

(65) Prior Publication Data
US 2014/0364744 A1    Dec. 11, 2014

(51) Int. Cl.
| | |
|---|---|
| *A61B 3/107* | (2006.01) |
| *A61B 3/00* | (2006.01) |
| *A61F 9/008* | (2006.01) |
| *A61F 9/009* | (2006.01) |
| *A61B 5/00* | (2006.01) |
| *A61B 3/10* | (2006.01) |
| *A61F 9/00* | (2006.01) |

(52) U.S. Cl.
CPC ............ *A61B 3/0083* (2013.01); *A61B 3/107* (2013.01); *A61B 5/0071* (2013.01); *A61F 9/009* (2013.01); *A61F 9/00802* (2013.01); *A61F 9/00825* (2013.01); *A61B 3/10* (2013.01); *A61F 9/008* (2013.01); *A61F 2009/0052* (2013.01); *A61F 2009/0087* (2013.01); *A61F 2009/00844* (2013.01); *A61F 2009/00872* (2013.01); *A61F 2250/0091* (2013.01)

(58) Field of Classification Search
CPC ......... A61B 3/10; A61B 3/107; A61B 5/0071; A61F 2009/0052; A61F 2009/0087; A61F 2009/00872; A61F 2250/0091; A61F 9/008
See application file for complete search history.

(56) References Cited

U.S. PATENT DOCUMENTS

| | | |
|---|---|---|
| 2004/0070761 A1 | 4/2004 | Horvath et al. |
| 2011/0319875 A1 | 12/2011 | Loesel et al. |

FOREIGN PATENT DOCUMENTS

| | | |
|---|---|---|
| EP | 1970034 A1 | 9/2008 |
| JP | 2005-246047 | 9/2005 |
| JP | 2009-505705 A | 2/2009 |
| JP | 2012-522542 | 9/2012 |
| WO | 02076355 A2 | 10/2002 |
| WO | 2011003431 A1 | 1/2011 |

*Primary Examiner* — Jennifer Dieterle
*Assistant Examiner* — Vani Gupta

(57) ABSTRACT

An apparatus and a method for cutting or ablating corneal tissue of an eye provide for detection of electromagnetic radiation exiting the eye. A detector is provided and coupled to a computer controlling the cutting or ablating laser radiation so that a two- or three-dimensional image of radiation exiting the eye can be generated.

19 Claims, 3 Drawing Sheets

APPARATUS, INTERFACE UNIT, SUCTION RING AND METHOD TO MONITOR CORNEAL TISSUE

CROSS REFERENCE TO RELATED APPLICATIONS

This application is a section 371 national stage phase of International Application No. PCT/EP2012/076300, filed 20 Dec. 2012, titled "APPARATUS, INTERFACE UNIT, SUCTION RING AND METHOD TO MONITOR CORNEAL TISSUE," which is hereby incorporated by reference in its entirety.

TECHNICAL FIELD

The present disclosure relates generally to corneal surgery, and more particularly to monitor Second Harmonic Generation (SHG), Third Harmonic Generation (THG), fluorescence radiation, and/or the plasma radiation to generate a model of a cornea of a patient.

BACKGROUND

In eye surgery, such as LASIK (laser-assisted in situ keratomileusis) surgery, information about the eye may be gathered for use in the surgery. For example, the shape or thickness of the corneal tissue before surgery or the depth of cuts made during surgery may be measured. As another example, images of any scars within the corneal tissue due to previous surgeries may be taken.

An apparatus for cutting corneal tissue of an eye according to the known art is disclosed e.g. in WO 2011/003431 A1. Such an apparatus typically comprises a so-called suction ring which can be placed on the eye and which is attached to the eye by generating a vacuum between the suction ring and the anterior surface of the eye. The suction ring unit serves to prevent unwanted movements of the eye during refractive surgery or any other treatment of the eye by laser radiation. The laser radiation is shaped and guided by an optical unit typically comprising several optical elements for guiding and focussing laser radiation relative to the eye, in particular, relative to corneal tissue of the eye that is to be cut.

It is understood that, beside of LASIK, the invention can be used in connection with tissue incisions in a human eye, e.g., in keratoplasty (e.g., anterior or posterior lamellar keratoplasty, penetrating keratoplasty in corneal graftings), in lenticule extraction for the purpose of refraction correction, in the cutting of intercorneal ring segments for the purpose of stabilising keratoconus and protrusion of the cornea (e.g., for the insertion of intacs, i.e. small implanted ring segments for biomechanical stabilisation of the cornea), in cataract incisions, in presbyopia incisions in the crystalline lens, in intrastromal inlays, in keratotomy for astigmatisms, in corneal resection and such like.

WO 02/076355 A2 describes a method for minimal-to-non-invasive optical treatment of tissues of an eye and for diagnosis thereof wherein a three-dimensional imaging of tissue is performed by means of radiation re-emitted from corneal tissue. The re-emission is generated by the laser system also used for ablation.

BRIEF SUMMARY

It is an object of the present invention to improve the imaging of corneal tissue.

Embodiments of the present invention are based on the finding that, before, during and/or afterwards of the corneal surgery, the impinging radiation generates electromagnetic radiation in the corneal tissue, which can be used to generate e.g., a three dimensional model of the cornea for diagnostic purpose or monitor the layer of the corneal tissue during incisions as well as reshapes of the stroma.

Such electromagnetic radiation exiting the eye in response to interaction of corneal tissue with pulsed laser radiation is e.g., SHG, fluorescence radiation, as well as THG and plasma radiation. The radiation pulses of the laser beam have a pulse duration in the nanosecond, picosecond, femtosecond or attosecond range.

An embodiment of the present invention is based on the finding that such radiation exiting the eye is of interest with regard to diagnostic purposes before, during and/or afterwards the refractive surgery. Although the intensity of such electromagnetic radiation exiting the eye is relatively low, in particular due to the non-linear character of its generation, it can be detected by photon counters.

If the electromagnetic radiation exiting the eye in response to the short-pulsed laser radiation before, during, or afterwards refractive surgery is generated within the corneal tissue, such radiation comprises information regarding substructures within the corneal tissue. The substructures may be three-dimensional. In this specification, the term "Second Harmonic Radiation" (SHR) is used for radiation that is generated by SHG. Analogously, the term "Third Harmonic Radiation" (THR) is used for radiation generated by THG during the refractive surgery.

For example, if during a scan of said laser radiation cutting or ablating corneal tissue, the SHR, THR, fluorescence or plasma radiation is detected by e.g. a photon counter, such detected signal can be processed to obtain e.g., a two-dimensional or three-dimensional image that can be displayed to the surgeon who may derive further information with regard to the treatment Because the position of the focussed spot of the cutting or ablating laser radiation is known, the position of the corneal tissue from which said electromagnetic radiation (SHR, THR, fluorescence, or plasma radiation) is emitted is also known, so that two-dimensional pictures of the latter radiation can be obtained from the signal generated by the photon counter, counting the photons of the SHR, THR, fluorescence, or plasma radiation. By performing this step at different layers of the cornea, i.e. at different depths in the cornea, three-dimensional pictures representing certain features of the cornea can be generated.

The electromagnetic radiation exiting the eye can be detected by reducing the influence of other unwanted signals by means of filters and/or by spatial discrimination, i.e. by positioning the detecting means at locations where primarily the SHR, THR, plasma and/or fluorescence radiation is received, but no or less other radiation that may disturb the signal to be detected.

The above-mentioned information comprised in the detected radiation exiting the eye can be obtained e.g., by empirical studies. For example, with corneal tissue comprising known substructures, such empirical information can be generated by cutting or ablating that corneal tissue with laser radiation and measuring the specific properties of the e.g. SHR, THR, fluorescence and/or plasma radiation detected as described above and processing the detected radiation to obtain said image of the radiation exiting the eye. Such images are generated empirically for many corneal tissues with known substructures (e.g., non-living eyes) to obtain an empirical "collection" of corneal substructures wherein the substructures generate certain images of e.g., SHR, THR, fluorescence and/or plasma radiation, so that, later on, during in vivo refractive surgery the obtained images of SHR, THR, and fluorescence radiation allow conclusions regarding the corneal substructures generating similar images.

Therefore, during in vivo refractive surgery said images generated by SHR, THR, plasma and/or fluorescence radiation can be displayed to the surgeon who may derive from such images conclusions regarding the properties of the treated corneal tissue.

The term "cutting" as used here covers in particular photonic disruption or laser inducted optical breakthroughs (LIOB) caused by focussed laser radiation at the focussed spot. The laser system used for such "cutting" can be operated at a reduced laser power, as compared to the laser power necessary for cutting or incision, in order to obtain a signal.

It is an object of the present invention to provide devices and methods for monitoring corneal tissue of an eye before, during or afterwards refractive surgery with enhanced usability with regard to analysis and/or diagnosis (e.g., by measurement, detection, calculation) of the corneal tissue.

For this purpose, embodiments of the invention provide an apparatus for monitoring corneal tissue of an eye comprising: a source emitting laser radiation, an optical unit for guiding and focussing said laser radiation relative to the corneal tissue, a suction ring unit adapted to be connected to the eye, and an interface unit adapted to be connected to the suction ring, wherein at least a part of said interface unit and/or at least a part of said suction ring is transparent or translucent for electromagnetic radiation exiting the eye.

Further embodiments may also provide a coupling unit connectable to said interface unit. Such a coupling unit may be connected between the interface unit and the suction ring or such a coupling unit may be connected in between the interface unit and an optical unit by which laser radiation is guided from the laser to the interface unit. Such an optional coupling unit may exhibit a special lens which functions e.g., as a filter element to block radiation having certain wavelengths whereas other wavelengths are transmitted through the lens such that this transmitted radiation can be detected.

The invention also provides a method for cutting or ablating corneal tissue of an eye, comprising the following steps: directing pulsed laser radiation onto the eye and monitoring the SHG, THR, fluorescence or plasma that is emitted from the eye and is caused by said pulsed laser radiation.

In the above wording "for cutting or ablating corneal tissue" the word "or" does not refer to an exclusive or, i.e. both the apparatus and the method can perform cutting and/or ablating corneal tissue. The cutting could also mean an incision which is typically performed by a FS-laser whereas ablating is typically performed by an Excimer laser. SHG and fluorescence radiation, according to an embodiment of the present invention, is performed at a lower power density level of the laser radiation as compared to cutting or ablating. The same laser system can be used at different levels of power density for the afore-mentioned applications, i.e. SHG or THG or fluorescence or plasma radiation, on the one hand, and cutting or ablating, on the other hand.

The above wording "exiting the eye" covers radiation exiting an anterior or exposed surface of the eye.

Embodiments of the invention utilize the finding that laser radiation of high power density applied during the above-mentioned procedures of refractive laser surgery generates SHG and the THG of the applied radiation. It is understood, beside of the plasma radiation or fluorescence, that this SHG and THG is generated non-linearly in an optical medium, e.g., the cornea, and develops also at the spot photodisruption or photoablation. Further it is understood that the fluorescence and SHG could also develop at the spot without photodisruption or photoablation.

In order to collect such electromagnetic radiation exiting the eye, at least a part of the interface unit or at least a part of the suction ring are made transparent or translucent for such radiation so that it can be detected by e.g., a photon counter arranged in the path of the radiation behind the suction ring or the interface unit. Depending on the design of the apparatus, both the interface unit and the suction ring may comprise said transparent sections, or one of them only. The electromagnetic radiation exiting the eye enters said transparent part at its distal end and exits said part at its proximal end. Also, one or more optical fibres can be used to guide the photons to the photon counter or other type of detector. If, in the context of this specification, a part of the suction ring or of the interface unit is mentioned wherein said part is transparent or translucent, this part is not the known aplanation plate that is used in the prior art for contacting and aplanating the cornea. Rather, if, in the context of this specification, said transparent or translucent part is mentioned, it refers to an element different from said aplanation plate that is also transparent and pressed against the cornea for flattening it. Rather, if in the context of this specification, it is referred to at least a part of the interface unit and/or of the suction ring, wherein said part is translucent or transparent, this means, according to embodiments of the invention, that the suction ring and/or the interface comprise a transparent or translucent part or element that is designed to collect radiation exiting the eye and to guide that collected radiation to a detector. According to Embodiments of the invention, the entire suction ring and/or the entire interface unit may be designed to collect and guide radiation exiting the eye in the afore-mentioned sense or parts of the suction ring and/or interface unit. According to embodiments of the invention, one or more fibres may be arranged within or at the suction ring and/or the interface unit to collect and guide radiation exiting the eye to guide the collected radiation to a detector. The detector may be a photon counter.

The radiation exiting the eye appears in time dependency on the timing of the laser radiation pulses generating SHR, THR, plasma radiation or fluorescence radiation. Accordingly, in order to improve the signal-to-noise ratio (SNR), the detector (e.g., photon counter) is controlled in time dependency from the laser pulses such that the time window for detection is open just when the desired signal photons are at and near their maximum.

Also, filters may be used in the path of the radiation to be detected such that photons not having the wavelength of SHR, THR, plasma radiation or fluorescence are prevented from entering the detector (photon counter).

Exemplary embodiments of the invention will be described in more detail in the following on the basis of the drawings.

Figure 1:
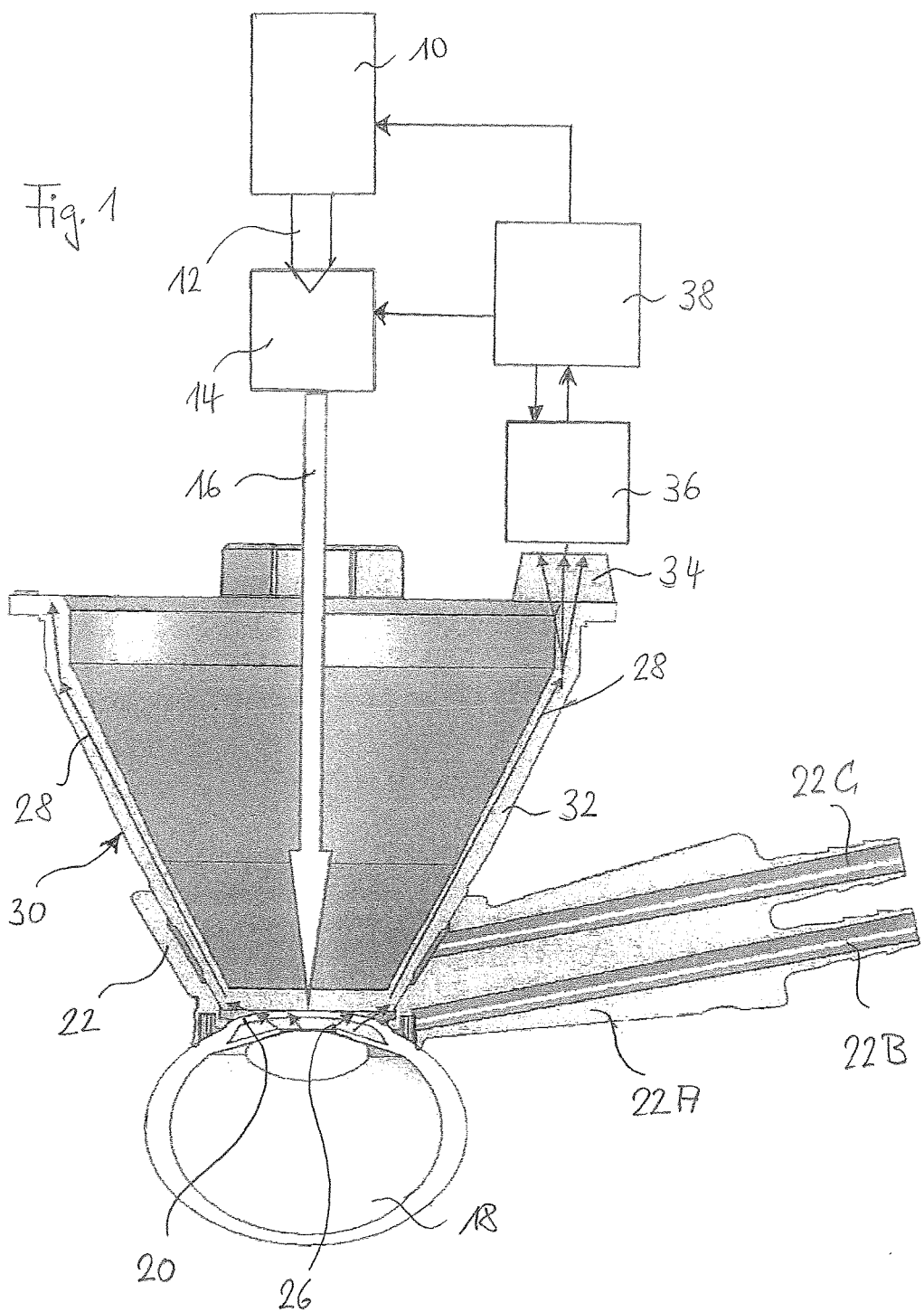
FIG. 1 shows schematically an apparatus for treating corneal tissue of an eye; this apparatus can also be used to generate short laser radiation pulses for generating one of the group comprising SHR, THR, plasma radiation, and fluorescence radiation.

As is shown in FIG. 1, an apparatus for monitoring, cutting and/or ablating corneal tissue of an eye comprises a laser source 10 emitting laser radiation 12 suitable for e.g. LASIK procedures. The laser radiation emitted by laser source 10 may comprise, after focussing, power densities suitable for monitoring, cutting or ablating corneal tissue.

An optical unit 14 forms and focuses the emitted laser radiation, as is known to a person skilled in the art of LASIK. The focused laser radiation 16 is scanned across the area of an eye 18 to be treated e.g., for monitoring, cutting a flap or for performing ablation of corneal tissue or other refractive procedures mentioned above. The radiation is focussed onto/into the eye's cornea 20.

A suction ring 22 is attached to the anterior surface of the cornea. To generate a vacuum between the suction ring and the cornea, a vacuum pipe 22B in a socket 22A of the suction ring 22 is connected to a vacuum pump (not shown).

An interface unit 30 is attached to the suction ring 22 also by vacuum, which is generated through vacuum pipe 22C connected to a vacuum pump (not shown).

Figure 3:
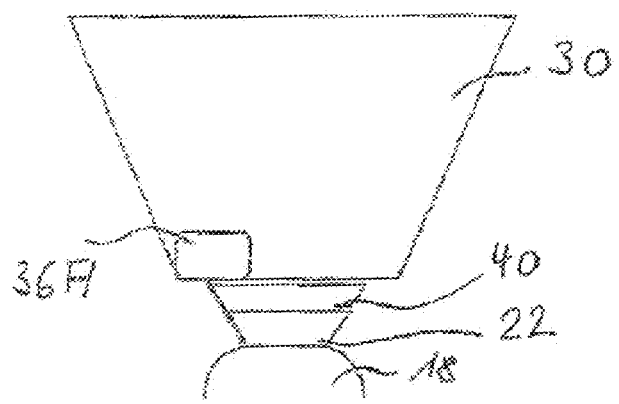
FIG. 3 shows schematically an arrangement of a detector in an apparatus according to FIG. 1 or 2.
Figure 4:
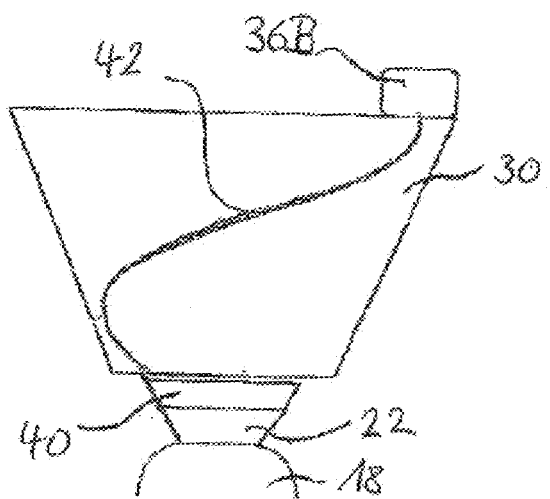
FIG. 4 shows another schematic example of an arrangement of a detector in an apparatus according to FIG. 1 or 2.

The interface unit 30 is sometimes called in the art an "eye cone". In the context of this specification, the term "interface unit" covers mechanical elements connected, directly or indirectly, to the suction ring 22. More specifically, the term "interface unit" also covers the so-called mechanical interface unit. According to embodiments of the invention, in addition to the suction ring and the interface unit, there may be a coupling unit 40 as shown in FIGS. 3 and 4. Such a coupling unit may be in between the suction ring 22 and the interface unit 30 (as shown in FIGS. 3 and 4) or, the coupling unit may be arranged in between the coupling unit 30 and the optical unit 14.

The focussed pulsed laser radiation 16 comprises, at its focus spot, sufficient power density in order to generate photodisruption or photoablation. Such photo disruptions or photoablation comprise a plasma that is suitable to generate, in a non-linear optical effect, the SHG and the THG of the impinging laser radiation, i.e. the radiation exiting the eye in response to the laser radiation having a wavelength of one half of the wavelength of the laser radiation and one third of the wavelength of the laser radiation, respectively.

Radiation with the afore-mentioned wavelengths is represented by arrows in FIG. 1. This radiation exits the eye 18 and enters a part 32, particularly the wall of the interface unit 30. This part 32 of the interface unit 30 is transparent and/or translucent with regard to the electromagnetic radiation 26 exiting the eye 18. The path of said radiation through part 32 of interface unit 30 is indicated by arrows 28 in FIG. 1. As is shown, the electromagnetic radiation exiting the eye 18 passes through a window 34 and enters a detector 36, e.g., a photon counter. Additional Filters (not shown) can be positioned in the path of said radiation in order to prevent radiation having unwanted wavelengths from entering the detector 36.

In the embodiment shown in FIG. 1, inside the conical wall of the interface unit 30, a beam path is provided for the radiation, indicated by arrows. The outer surface of said wall may be coated to prevent any radiation other than the radiation 26 exiting the eye from entering the beam path. Also, the internal surfaces of the walls of the interface unit 30 may be coated with a reflecting surface, such that the photons exiting the eye are guided with minimum loss of intensity to the detector 36.

A computer 38 controls both the laser source 10 and the optical unit 14, in particular with regard to the timing of the laser pulses and the scanning of the focussed laser spot relative to the cornea 20. Therefore, computer 38 "knows" the position where the electromagnetic radiation 26 is generated so that the computer can generate a map on which the photons counted by detector 36 are co-ordinated to the position in the cornea where the SHG, the THG, the plasma or the fluorescence radiation, depending on how the detector is adjusted for monitoring, are generated.

By mapping different layers in the cornea, a three-dimensional image can be generated representing the three-dimensional emission of the SHG, THG, plasma and/or fluorescence radiation, respectively. Said image can be displayed to the surgeon, who may use the image to derive conclusions regarding the substructures within the treated cornea.

Figure 2:
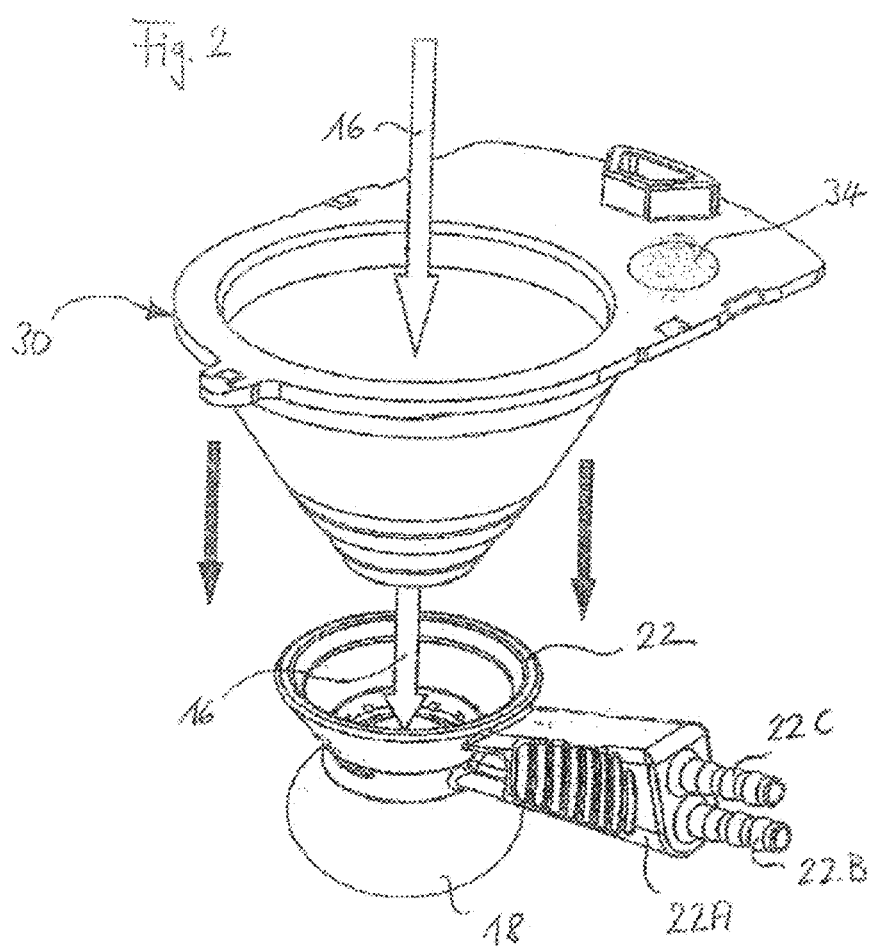
FIG. 2 shows a suction ring and the interface unit of an apparatus according to FIG. 1 in exploded representation.

FIG. 2 shows a suction ring 22 and interface unit in exploded representation. In the drawings, subject-matter of the same or similar nature is denoted by identical reference numerals so that a repeated description is not necessary.

FIG. 3 shows an embodiment of an apparatus for diagnosis and/or cutting and/or ablating of corneal tissue of an eye wherein, in addition to what is shown in FIGS. 1 and 2, a coupling unit 40 is provided in between the suction ring 22 and the interface unit 30. Whether or not the apparatus comprises, in addition to the suction ring 22, a coupling unit or whether the interface unit 30 is coupled directly to the suction ring 22, depends on the particular design of the apparatus. According to embodiments of the present invention, said part that is transparent or translucent for electromagnetic radiation 26 exiting the eye 18 can be part of the suction ring 22 and/or the coupling unit 40 (if any), and/or of the interface unit 30.

In the embodiment shown in FIG. 3, a detector 36a (corresponding to the detector 36 described above) is arranged directly above the coupling unit 40 at the distal end of the interface unit 30.

In the embodiment shown in FIG. 3, a coupling unit 40 is arranged in between the suction ring 22 and the interface unit 30. Alternatively, according to the particular design of the apparatus, a coupling unit may also be arranged on the other side of the interface unit 30, i.e. in between the interface unit 30 and the optical unit 14.

In the embodiment shown in FIG. 4, a detector 36B is arranged at the proximal end of the interface unit 30. Optical fibres 42 guide the photons which are to be detected from the distal end of interface unit 30 to the detector 36B.

The invention claimed is:

1. An apparatus for treating corneal tissue of an eye, the apparatus comprising:
   a source configured to emit pulsed laser radiation;
   an optical unit configured to guide and focus the laser radiation relative to the corneal tissue;
   a detector configured to detect electromagnetic radiation exiting the eye;
   a suction ring unit adapted to be connected to the eye; and
   an interface unit adapted to be coupled to the suction ring, the interface unit having a conical wall defining a cavity within a structural component of the conical wall, wherein the focused laser radiation from the optical unit is guided through the cavity toward the corneal tissue, and wherein the structural component of the conical wall contains an internal beam path to guide the electromagnetic radiation exiting the eye towards the detector.

2. The apparatus according to claim 1, wherein the electromagnetic radiation exiting the eye has a wavelength shorter than the wavelength of the pulsed laser radiation.

3. The apparatus according to claim 1, wherein the source of laser radiation emits laser pulses in the nanosecond, picosecond, femtosecond, or attosecond range.

4. The apparatus according to claim 1, the detector performing time dependent detection of the electromagnetic radiation.

5. A method for monitoring corneal tissue of an eye, the method comprising:
attaching an interface unit to a suction ring that is attached to the eye, the interface unit having a conical wall defining a cavity within a structural component of the conical wall;
directing pulsed laser radiation through the cavity onto or into the eye to generate electromagnetic radiation that exits the eye;
collecting the electromagnetic radiation that exits the eye in a beam path internal to the structural component of the interface unit;
guiding the electromagnetic radiation along the beam path internal to the structural component of the interface unit towards a detector; and
detecting the radiation with the detector.

6. The method according to claim 5 wherein the collected radiation is collected before, during, or after a surgical treatment of the eye.

7. The apparatus of claim 1, wherein the detector is offset from the optical unit by a distance substantially equal to a radius of a top of the interface unit such that the detector is axially aligned with an upper portion of the structural component of the conical wall.

8. The apparatus of claim 7, further comprising a window on the upper portion of the structural component of the conical wall that allows the electromagnetic radiation exiting the eye and traveling through the internal beam path to exit the structural component of the conical wall.

9. The apparatus of claim 1, wherein, the electromagnetic radiation exiting the eye comprises at least one of Second Harmonic Radiation (SHR), Third Harmonic Radiation (THR), plasma radiation, and fluorescence radiation caused by the laser radiation.

10. The apparatus of claim 9, wherein the interface unit is substantially transparent to the Second Harmonic Radiation (SHR), Third Harmonic Radiation (THR), plasma radiation, or fluorescence radiation caused by the laser radiation.

11. The apparatus of claim 1, wherein an outer surface of the structural component of the conical wall is coated with a material that prevents radiation from another source from entering the internal beam path.

12. The apparatus of claim 1, wherein an internal surface of the structural component of the conical wall is coated with a reflecting material that reduces a loss of intensity of the radiation exiting the eye.

13. The apparatus of claim 1, wherein an internal surface of the structural component of the conical wall further includes one or more filter to prevent one or more wavelength of the radiation exiting the eye to reach the detector.

14. The method for monitoring corneal tissue of an eye of claim 5, further comprising positioning the detector offset from the optical unit by a distance substantially equal to a radius of a top of the interface unit such that the detector is axially aligned with an upper portion of the structural component of the conical wall.

15. The method for monitoring corneal tissue of an eye of claim 14, wherein an upper portion of the structural component of the conical wall includes a window that allows the electromagnetic radiation exiting the eye and traveling through the internal beam path to exit the structural component of the conical wall.

16. The method for monitoring corneal tissue of an eye of claim 5, wherein, the electromagnetic radiation exiting the eye comprises at least one of Second Harmonic Radiation (SHR), Third Harmonic Radiation (THR), plasma radiation, and fluorescence radiation caused by the laser radiation, and wherein the interface unit is substantially transparent to the Second Harmonic Radiation (SHR), Third Harmonic Radiation (THR), plasma radiation, or fluorescence radiation caused by the laser radiation.

17. The method for monitoring corneal tissue of an eye of claim 5, wherein an outer surface of the structural component of the conical wall is coated with a material that prevents radiation from another source from entering the internal beam path.

18. The method for monitoring corneal tissue of an eye of claim 5, wherein an internal surface of the structural component of the conical wall is coated with a reflecting material that reduces a loss of intensity of the radiation exiting the eye.

19. The method for monitoring corneal tissue of an eye of claim 5, wherein an internal surface of the structural component of the conical wall further includes one or more filter to prevent one or more wavelength of the radiation exiting the eye to reach the detector.

* * * * *